US012727764B2

(12) United States Patent
Sayama

(10) Patent No.: US 12,727,764 B2
(45) Date of Patent: Sep. 8, 2026

(54) DENTAL CARIES DETECTION DEVICE

(71) Applicant: Tamron Co., Ltd., Saitama (JP)

(72) Inventor: Atsushi Sayama, Saitama (JP)

(73) Assignee: TAMRON CO., LTD., Saitama (JP)

( * ) Notice: Subject to any disclaimer, the term of this patent is extended or adjusted under 35 U.S.C. 154(b) by 246 days.

(21) Appl. No.: 18/596,886

(22) Filed: Mar. 6, 2024

(65) Prior Publication Data

US 2024/0315565 A1 Sep. 26, 2024

(30) Foreign Application Priority Data

Mar. 24, 2023 (JP) ................................ 2023-048743

(51) Int. Cl.
*A61B 5/00* (2006.01)
*G06T 7/00* (2017.01)

(52) U.S. Cl.
CPC .......... *A61B 5/0088* (2013.01); *A61B 5/7445* (2013.01); *G06T 7/00* (2013.01); *G06T 2207/30036* (2013.01)

(58) Field of Classification Search
CPC .......... G02B 2027/0178; G02B 27/017; G02B 27/0093; G02B 2027/014; G02B 2027/0187; G02B 2027/0118; G02B 27/0172; G02B 5/30; G02B 2027/0138; G02B 27/0176; G02B 26/12; G02B 27/48; G02B 6/3604; G02B 2027/0147; G02B 2027/0112; G02B 2027/0127; G02B 2027/0132; G02B 27/0149; G02B 5/18; G02B 6/12009; G02B 2027/011; G02B 2027/0123; G02B 2027/0134; G02B 2207/113; G02B 2207/115; G02B 5/23; G02B 5/3058; G02B 6/0038; G02B 6/0045; G02B 6/0053; G02B 6/0056;
(Continued)

(56) References Cited

U.S. PATENT DOCUMENTS

2006/0238745 A1* 10/2006 Hashimoto ............ G01N 21/65 356/73
2015/0260650 A1 9/2015 Ashrafi et al.
(Continued)

FOREIGN PATENT DOCUMENTS

JP 2018-521701 A 8/2018
JP 2019-510202 A 4/2019

OTHER PUBLICATIONS

Alex C.-T. Ko, Lin-P'ing Choo-Smith, Mark Hewko, Michael G. Sowa, Cecilia C.S. Dong, and Blaine Cleghorn, "Detection of early dental caries using polarized Raman spectroscopy," Opt. Express 14, 203-215 (Year: 2006).*
(Continued)

*Primary Examiner* — Alex Kok S Liew
(74) *Attorney, Agent, or Firm* — Paratus Law Group, PLLC

(57) ABSTRACT

A tooth of a subject is irradiated with light having a specific polarization direction, and each of two or more polarization components in Raman-scattered light from the tooth is separated by a polarization separation element and detected by a detector. Polarization anisotropy of the Raman-scattered light is obtained from a detection signal of each polarization component, and dental caries in the tooth is detected based on the polarization anisotropy.

12 Claims, 11 Drawing Sheets

(58) Field of Classification Search
CPC ............... G02B 6/12019; G02B 7/008; G02B 21/0032; G02B 21/0076; G02B 21/361; G02B 5/04; G02B 5/1842; G02B 5/28; G06F 3/013; G06F 3/017; G06F 1/163; G06F 3/005; G06F 3/011; G06F 3/03547; G06F 3/04815; G06F 13/00; G06F 3/012; G06F 3/014; G06F 3/0227; G06F 3/0346; G06F 3/0488
See application file for complete search history.

(56) References Cited

U.S. PATENT DOCUMENTS

2018/0146857 A1 5/2018 González Fernández et al.
2018/0235738 A1* 8/2018 Atiya .................. A61C 9/0053

OTHER PUBLICATIONS

Ko et al., Detection of early dental caries using polarized Raman spectroscopy, Optics Express 203, Jan. 9, 2006, pp. 1-13, vol. 14, No. 1.

Bulatov et al., Dental Enamel Caries (Early) Diagnosis and Mapping by Laser Raman Spectral Imaging, Instrumentation Science and Technology, Mar. 18, 2008, pp. 235-244, vol. 36.

* cited by examiner

DENTAL CARIES DETECTION DEVICE

CROSS-REFERENCE TO RELATED APPLICATIONS

This application is based on and claims the benefit of priority from Japanese Patent Application No. 2023-048743, filed on Mar. 24, 2023, the entire contents of which are incorporated herein by reference.

BACKGROUND OF THE INVENTION

Technical Field

The present invention relates to a dental caries detection device.

Related Art

In recent years, it has been revealed that early dental caries can be treated without grinding the tooth, and the concept of preventive dentistry that prevents dental caries progression has attracted attention. Therefore, a technology for accurately detecting early dental caries is desired. In such a background, a technology using Raman spectroscopy for detecting dental caries is known (see, for example, JP 2019-510202 A, JP 2018-521701 A, "Detection of early dental caries using polarized Raman spectroscopy (Alex C.-T. Ko et. al., OPTICS EXPRESS, Vol. 14, No. 1, p. 203-215, 2006)", and "Dental Enamel Caries (Early) Diagnosis and Mapping by Laser Raman Spectral Imaging (Valery Bulatov et. al., Instrumentation Science and Technology, 36, p. 235-244, 2008)".

In Raman spectroscopy for a tooth, both Raman signals from a component constituting the tooth and a component attached on the tooth are included in a Raman spectrum. The Raman signals are different from one another depending on individuals, and are also different depending on a measurement point of an individual tooth. Therefore, it is usually necessary to perform spectral analysis in order to extract spectral information of a specific component from the Raman spectrum of the tooth. Since the spectral analysis is based on expert knowledge, it is difficult for a dentist to perform the spectral analysis in real time at the time of examination. In addition, in a case where a computational function or an auxiliary device configuration are further provided for reducing and/or simplifying such difficult analysis, a configuration of a detection device becomes complicated and/or the size of the detection device increases, which may lead to an increase in cost of the detection device.

JP 2019-510202 A does not disclose a specific method for actual diagnosis of dental caries. In the technology described in "Detection of early dental caries using polarized Raman spectroscopy (Alex C.-T. Ko et. al., OPTICS EXPRESS, Vol. 14, No. 1, p. 203-215, 2006)", dental caries in teeth is detected by polarized Raman spectroscopy, which the incident light and the Raman-scattered light have a specific polarization direction, and the technology described in "Dental Enamel Caries (Early) Diagnosis and Mapping by Laser Raman Spectral Imaging (Valery Bulatov et. al., Instrumentation Science and Technology, 36, p. 235-244, 2008)" is a technology for detecting dental caries by Raman spectroscopy. However, these literatures do not disclose a reduction and/or simplification of spectral analysis for dental caries detection.

In addition, in the technology described in JP 2018-521701 A, areas of a plurality of peaks observed at different wavelengths in a Raman spectrum of a tooth are calculated, and a ratio therebetween is calculated to try to evaluate demineralization and remineralization of the tooth, that is, caries. Further, in the evaluation, a numerical value obtained from studies about a normal tooth part is compared with the detected value. Therefore, reliability of the inspection result may also be affected by fluctuation of the detected value depending on individual differences and/or a measurement point.

As described above, in the related art, there is still room for considering the above problems associated with spectral analysis in detection of dental caries.

An object of one aspect of the present invention is to provide a technology capable of clearly and easily detecting dental caries when diagnosing dental caries by Raman spectroscopy.

In order to solve the above problems, a dental caries detection device according to one aspect of the present invention includes: a light source configured to emit light having a first polarization direction; a polarization separation unit configured to separate the light having the first polarization direction and other light having a second polarization direction in Raman-scattered light from a tooth of a subject irradiated with the light having the first polarization direction; a detector configured to detect each of the light having the first polarization direction and the light having the second polarization direction separated by the polarization separation unit; and an anisotropy acquisition unit configured to obtain polarization anisotropy of the Raman-scattered light from a detection signal of each of the light having the first polarization direction and the light having the second polarization direction from the detector.

SUMMARY OF THE INVENTION

According to one aspect of the present invention, it is possible to clearly and easily detect dental caries when diagnosing dental caries by Raman spectroscopy.

DESCRIPTION OF THE EMBODIMENTS

In embodiments of the present invention, a part suspected of having dental caries (also referred to as "suspected carious part") in a tooth to be measured is irradiated with light, Raman-scattered light generated from the suspected carious part is separated for each polarization component, and dental caries is detected with reference to an intensity of the separated polarization components. Hereinafter, the embodiments of the present invention will be described.

First Embodiment

Configuration of Device

Figure 1:
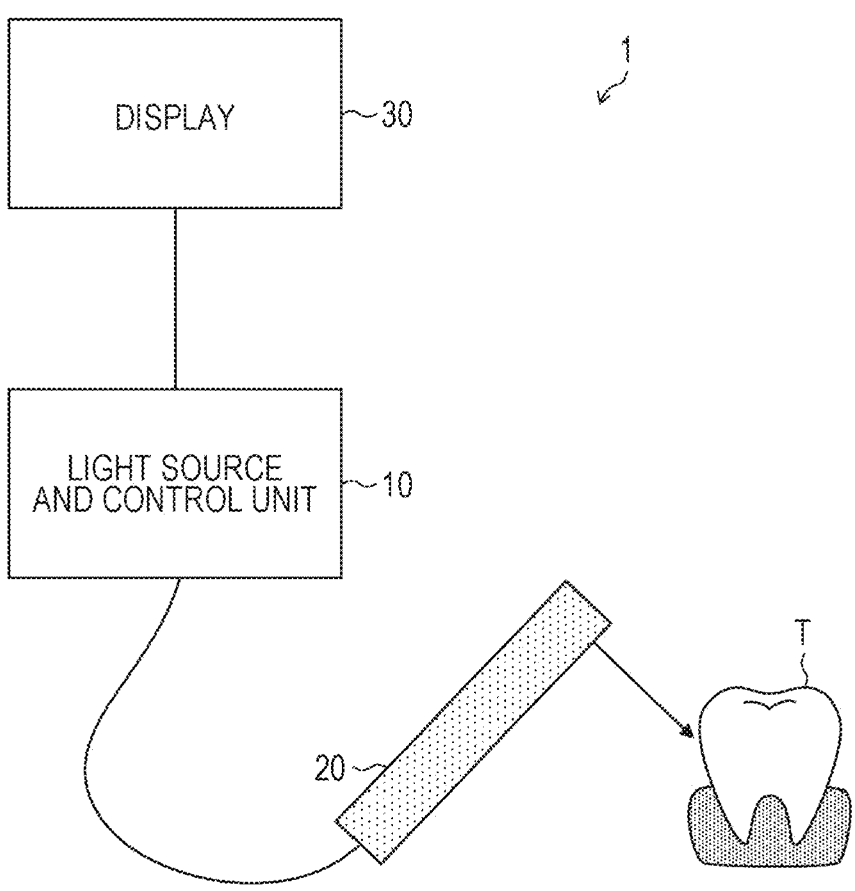
FIG. 1 is a diagram schematically illustrating an overall configuration of a dental caries detection device according to a first embodiment of the present invention.

FIG. 1 is a diagram schematically illustrating an overall configuration of a dental caries detection device according to the present embodiment. As illustrated in FIG. 1, a dental caries detection device 1 includes a device main body 10, an intraoral insertion portion 20, and a display device 30.

The device main body 10 includes a part of a detection optical system for detecting dental caries, and an information processing device for executing processing of detecting dental caries. For example, the device main body 10 includes a light source, a detector, and various optical elements as a part of the detection optical system, and the information processing device includes a control unit for controlling various devices and executing signal computation processing, and a functional configuration therefor. The control unit is, for example, a processor, and implements desired control by a program for functioning as a specific control block.

Figure 2:
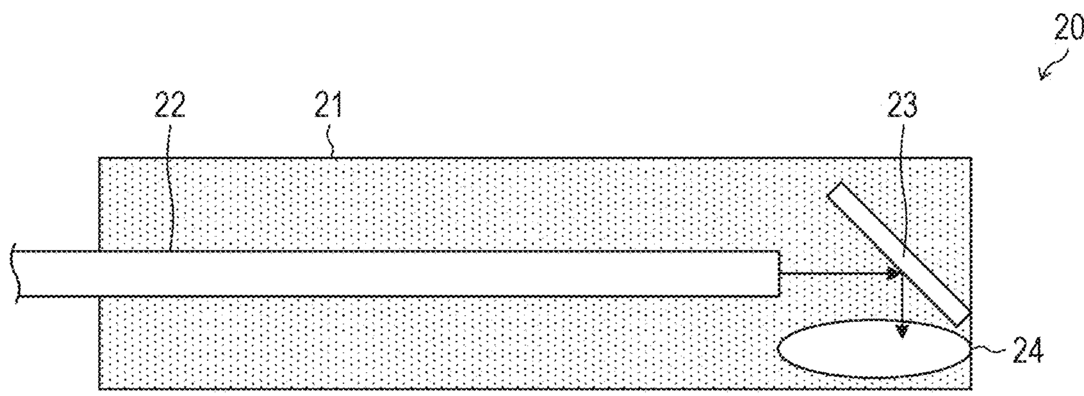
FIG. 2 is a diagram schematically illustrating a configuration of an intraoral insertion portion in the first embodiment of the present invention.

As schematically illustrated in FIG. 2, the intraoral insertion portion 20 includes a case 21, an optical fiber 22, a mirror 23, and a lens 24. The intraoral insertion portion 20 is a part of the above-described detection optical system.

The case 21 is a hollow housing having a shape suitable for insertion into an oral cavity of a subject whose tooth is to be examined, for example, a substantially cylindrical shape. The optical fiber 22 transmits light from the light source of the device main body 10 toward the tooth and transmits scattered light from the tooth to the device main body 10. The mirror 23 adjusts a transmission direction of the light between the optical fiber 22 and the lens 24 to form a light transmission path between the optical fiber 22 and the lens 24.

The lens 24 focuses the light from the optical fiber 22 on a tooth T. The lens 24 focuses the scattered light from the tooth T on the mirror 23. The lens 24 is an example of an optical element that exhibits such a function, and may be a single lens, a liquid lens, or a variable-focus lens system including a plurality of lenses. The lens 24 is preferably a liquid lens from the viewpoint of easily adjusting a focal length of irradiation light for the tooth T.

Furthermore, the intraoral insertion portion 20 further includes a shake-compensation mechanism that substantially cancels an influence of shakes of the intraoral insertion portion 20. The shake-compensation mechanism includes, for example, a coil and a magnet, similarly to a shake-compensation mechanism of a zoom lens. The shake-compensation mechanism moves the optical element (such as the mirror 23 or the lens 24) in the intraoral insertion portion 20 in a direction perpendicular to an optical axis of the irradiation light or scattered light and in a direction to cancel the shakes, thereby reducing an influence of the shakes. Such movement of the intraoral insertion portion 20 can be detected using, for example, a gyro sensor that detects an angular velocity of the intraoral insertion portion 20.

The display device 30 is a device for displaying various types of information such as a captured image and information related to a detection operation to an operator of the intraoral insertion portion 20. Examples of the display device 30 include a liquid crystal display device and an organic electroluminescence (EL) display device. The display device 30 may further have a touch panel function, and such a display device 30 also serves as an input device.

Figure 3:
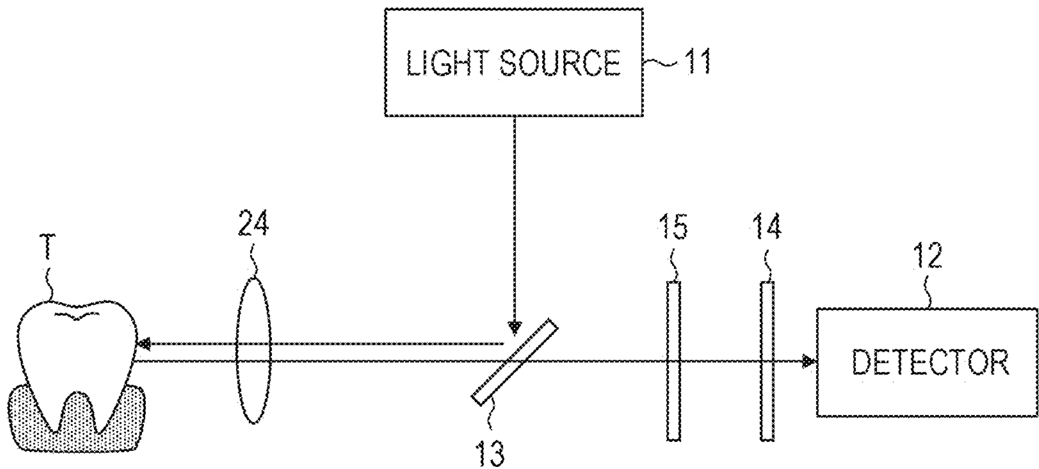
FIG. 3 is a diagram schematically illustrating a main part of a configuration of a detection optical system of the dental caries detection device according to the first embodiment of the present invention.

FIG. 3 is a diagram schematically illustrating a main part of a configuration of a detection optical system of the dental caries detection device 1. As illustrated in FIG. 3, the optical system includes a light source 11, a detector 12, an optical filter 13, a polarization separation element 14, a bandpass filter 15, and a lens 24. These components constitute the above-described detection optical system. The detection optical system includes an irradiation optical system and a light receiving optical system. The irradiation optical system includes the light source 11, the optical filter 13, and the lens 24. Although not illustrated in FIG. 3, the optical fiber 22 and the mirror 23 described above are included between the optical filter 13 and the lens 24. The light receiving optical system includes the lens 24, the optical filter 13, the bandpass filter 15, the polarization separation element 14, and the detector 12.

The light source 11 emits light having a first polarization direction and with which the tooth T of the subject is to be irradiated. The light emitted from the light source 11 is light that generates Raman-scattered light of a component that changes depending on the presence or absence of dental caries when the tooth T is irradiated. The "component that changes depending on the presence or absence of dental caries" is, for example, a component that constitutes the tooth T and whose state changes due to dental caries, and specific examples thereof include hydroxyapatite. Alternatively, the "component that changes depending on the presence or absence of dental caries" is a component caused by dental caries, and specific examples thereof include acid. In the present embodiment, hydroxyapatite of the tooth T is detected by polarized Raman spectroscopy.

The light generated by the light source 11 is, for example, visible light or near-infrared light having a partial wavelength in a wavelength range of 300 to 800 nm. A high-output light source such as a diode laser or a fiber laser is used as the light source 11. The light source 11 may be a wavelength-tunable light source. In the present embodiment, hydroxyapatite is detected as described above, and thus, a laser having a wavelength of 785 nm is used as the light source 11.

The light having the first polarization direction emitted from the light source 11 is not limited, but is linearly polarized light in the present embodiment. Normally, linearly polarized light is output from a laser light source. Therefore, in a case where the light source 11 is a laser, the light having the first polarization direction is light emitted from the light source 11. In a case where the light source 11 does not output linearly polarized light, a polarizer is disposed on an optical path of light emitted from the light source 11 to generate the light having the first polarization direction.

The optical filter 13 is an optical element that reflects the light from the light source 11 and transmits the Raman-scattered light from the tooth T. The optical filter 13 can be appropriately set based on various conditions such as arrangement of the optical elements in the detection optical system, the wavelength of the light from the light source 11, and the wavelength of the Raman-scattered light from the tooth T. Examples of the optical filter 13 include an edge filter and a notch filter.

The bandpass filter 15 is an optical element that transmits light in a specific wavelength region in the Raman-scattered light from the tooth T. The bandpass filter 15 is disposed closer to the detector 12 than the optical filter 13 in the light receiving optical system. The bandpass filter 15 can be designed to transmit a specific wavelength depending on the wavelength of the light source 11 and a detection target in the tooth T. A peak wavelength of the Raman-scattered light derived from hydroxyapatite when the tooth T is irradiated with the 785-nm-light from the light source 11 is about 850 nm. In the present embodiment, the bandpass filter 15 is an optical element that transmits light having a wavelength of 800 to 900 nm, for example.

The polarization separation element 14 is an optical element that separates and transmits the light having the first polarization direction (linearly polarized light, for example, p-polarized light) and other light having a second polarization direction (linearly polarized light, for example s-polarized light) in the Raman-scattered light from the tooth. In the present embodiment, the polarization separation element 14 is a polarizer that transmits linearly polarized light and blocks polarization components of other directions, and is a polarizer arranged in such a way as to be rotatable around an optical axis in the light receiving optical system. By rotating the polarization separation element 14 by 90° (for example, continuous rotation or intermittent rotation), it is possible to transmit each of first linearly polarized light in the light from the light source 11 and second linearly polarized light polarized in a direction orthogonal to the first linearly polarized light. The polarization separation element 14 is one aspect of a polarization separation unit that separates the light having the first polarization direction and the other light having the second polarization direction in the Raman-scattered light.

The detector 12 is an optical sensor capable of detecting the Raman-scattered light, and detects each of the light having the first polarization direction and the light having the second polarization direction separated by the polarization separation element 14. Examples of the detector 12 include a spectrometer, an image sensor, and a photomultiplier tube. Examples of the image sensor include a complementary metal-oxide semiconductor (CMOS) sensor and a charge coupled device (CCD) sensor. In the present embodiment, the detector 12 is a spectrometer. A signal of the Raman-scattered light detected by the detector 12 is output to the control unit of the above-described information processing device of the device main body 10.

Dental Caries Detection

Figure 4:
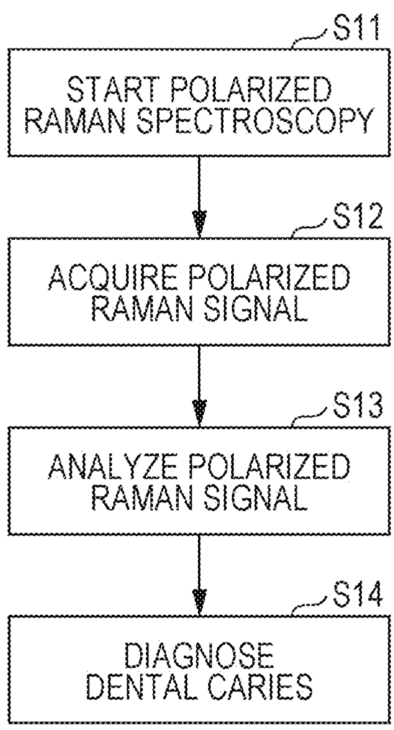
FIG. 4 is a diagram showing an example of a flow of processing of detecting dental caries in the dental caries detection device according to the first embodiment of the present invention.

Next, detection of dental caries in the present embodiment will be described. FIG. 4 is a diagram showing an example of a flow of processing of detecting dental caries in the dental caries detection device 1.

In step S11, the control unit of the above-described information processing device of the device main body 10 starts the polarized Raman spectroscopy. The control unit causes the light source 11 to emit the light having the first polarization direction.

The operator (for example, a dentist) of the intraoral insertion portion 20 inserts the intraoral insertion portion 20 into the mouth of the subject (for example, a patient), irradiates the tooth T of the subject with the light from the light source 11 while performing scanning at a speed of several seconds for each part, and simultaneously obtains the Raman-scattered light from the irradiated part of the tooth T. At this time, the hand of the operator may shake, but shakes of the intraoral insertion portion 20 caused by the shakes of the hand of the operator are reduced by the shake-compensation mechanism described above and are thus substantially canceled.

In step S12, the control unit obtains a polarized Raman signal. The control unit drives the polarization separation element 14 to rotate by 90° at specific intervals, and sequentially obtains detected values of the light having the first polarization direction and the light having the second polarization direction that have been transmitted through the polarization separation element 14 and have reached the detector 12. Hereinafter, in the light reaching the detector 12, a component of light having the same polarization direction as the light from the light source 11 (the light having the first polarization direction) is also referred to as a "parallel component", and a component of light having a polarization direction orthogonal to the first polarization direction (the light having the second polarization direction) is also referred to as an "orthogonal component". In this way, the control unit obtains a signal of the parallel component and a signal of the orthogonal component of the Raman-scattered light detected by the detector 12.

In step S13, the control unit analyzes the polarized Raman signal. The control unit obtains polarization anisotropy of the Raman-scattered light detected by the detector 12 from the signal of the parallel component and the signal of the orthogonal component obtained from the detector 12. Here, the polarization anisotropy will be described.

Figure 5:
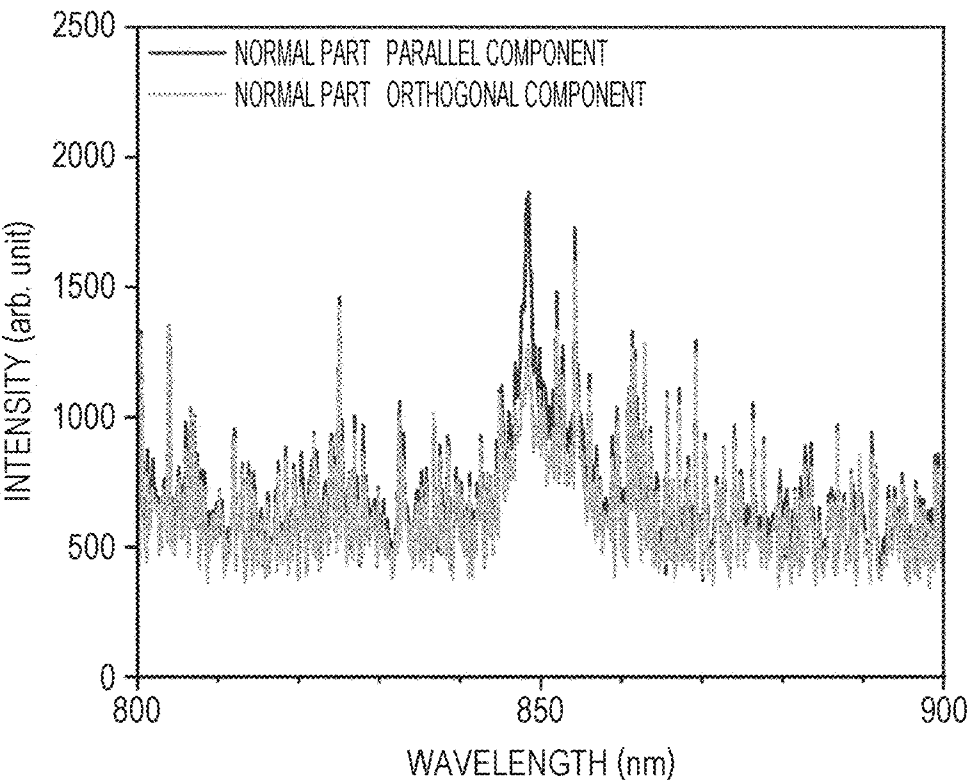
FIG. 5 is a diagram showing an example of a detection result for each polarization component at a normal part of a tooth when the tooth is analyzed by polarized Raman spectroscopy in the first embodiment of the present invention.
Figure 6:
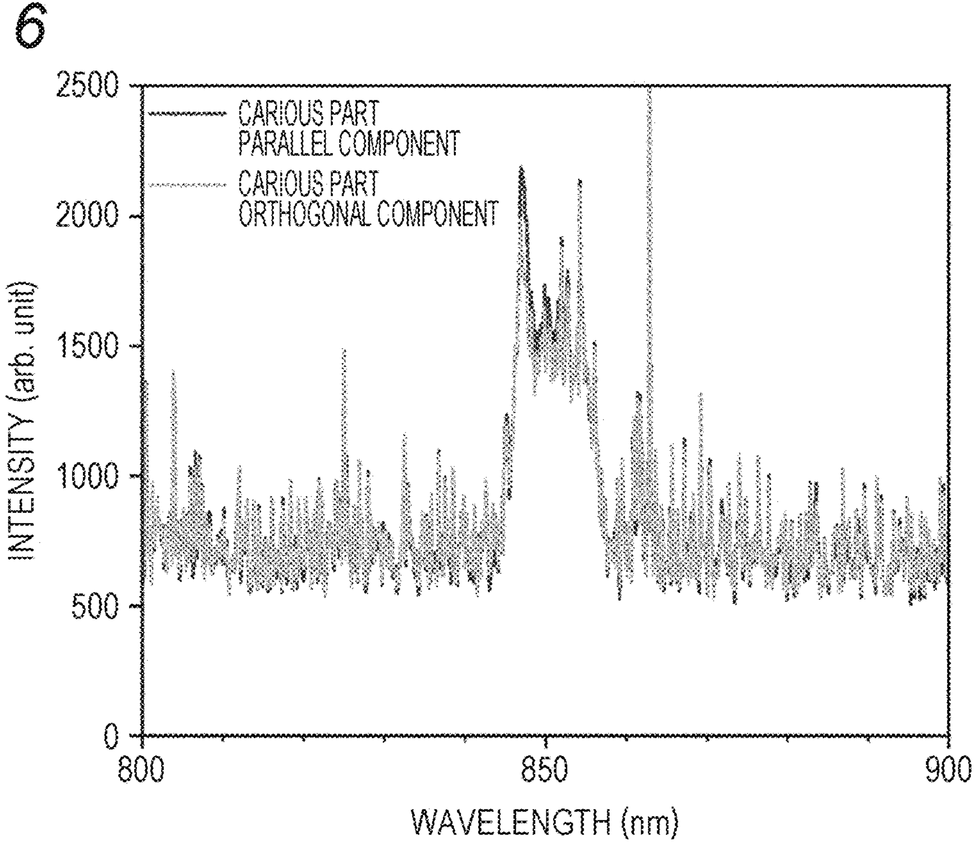
FIG. 6 is a diagram showing an example of a detection result for each polarization component at a carious part of the tooth when the tooth is analyzed by the polarized Raman spectroscopy in the first embodiment of the present invention.

FIG. 5 shows an example of a detection result for each polarization component at a normal part of the tooth T when the tooth T is analyzed by the polarized Raman spectroscopy in the present embodiment, and FIG. 6 shows an example of a detection result for each polarization component at a carious part of the tooth T. In FIGS. 5 and 6, a peak is observed at about 850 nm. The peak of Raman signals in FIG. 5 and FIG. 6 is derived from hydroxyapatite of the tooth. As is clear from FIG. 5, at the normal part of the tooth T, the polarization component (parallel component) of the light from the light source 11 is detected stronger than the orthogonal component at 850 nm. As described above, strong polarization dependence of the signal derived from hydroxyapatite is shown in the polarized Raman spectroscopy for the tooth T.

On the other hand, at the carious part, as is clear from FIG. 6, a difference between the peaks of the parallel component and the orthogonal component at 850 nm is not as large as that at the normal part, and is unclear. In addition, as is clear from FIGS. 5 and 6, a detection signal of the Raman-scattered light includes an influence of fluorescence or the like, and the Raman-scattered light is obtained by scanning the tooth T, which makes the baseline less stable. As a result of which, it is more difficult to determine the peak of hydroxyapatite around 850 nm.

Figure 7:
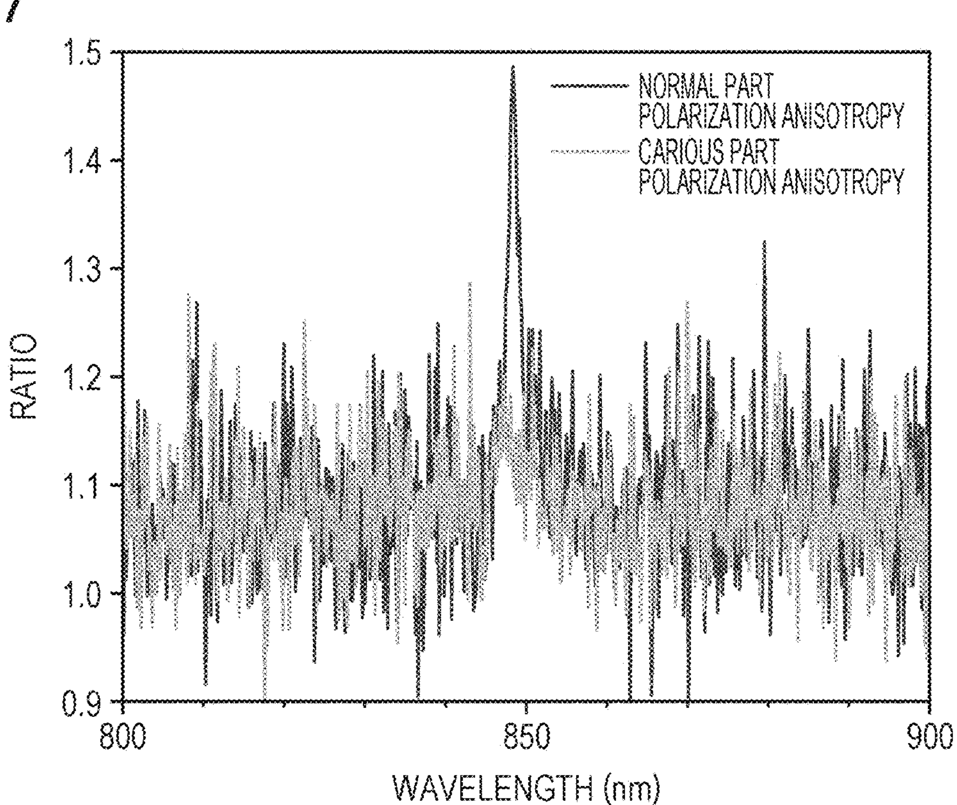
FIG. 7 is a diagram showing an example of polarization anisotropy of the normal part and polarization anisotropy of the carious part of the tooth when the tooth is analyzed by the polarized Raman spectroscopy in the first embodiment of the present invention.

FIG. 7 is a diagram showing an example of the polarization anisotropy of the normal part and the polarization anisotropy of the carious part of the tooth when the tooth T is analyzed by the polarized Raman spectroscopy in the present embodiment. The polarization anisotropy of the normal part and the polarization anisotropy of the carious part are obtained from the results of the parallel component and the orthogonal component as shown in FIGS. 5 and 6. The polarization anisotropy is a ratio (I1/I2) of a detected intensity (I1) of the parallel component to a detected intensity (I2) of the orthogonal component. In FIG. 7, the polarization anisotropy of the carious part clearly indicates that a difference in intensity between the parallel component and the orthogonal component at the carious part is small, and the polarization anisotropy of the normal part clearly indicates that a difference in intensity between the parallel component and the orthogonal component is large. Therefore, the difference between the normal part and the carious part becomes clearer, and determination of the carious part becomes easier.

In the present embodiment, the polarization anisotropy of the Raman-scattered light is obtained from the parallel component and the orthogonal component as described above. The control unit in the present embodiment corresponds to an anisotropy detection unit that obtains the polarization anisotropy of the Raman-scattered light from detection signals of the parallel component and the orthogonal component from the detector 12.

In step S14, the control unit performs control for diagnosis of dental caries. For example, the control unit may output a diagnosis result indicating that there is a suspicion of dental caries when the polarization anisotropy of the peak at, for example, 850 nm is in a specific range that can be said to be substantially 1 from the result of the polarization anisotropy. Alternatively, the control unit may display a result of acquiring the polarization anisotropy on the display device 30 in the form of a graph as illustrated in FIG. 7 for diagnosis of dental caries by a dentist.

Major Operation and Advantageous Effects

In the present embodiment, the polarization anisotropy is obtained from the Raman-scattered light from the tooth T. A change of the tooth T before and after dental caries is detected by Raman spectroscopy, and the change is further emphasized by acquisition of the polarization anisotropy. Therefore, it is possible to easily detect and determine dental caries as compared with the related art.

The present embodiment includes the bandpass filter 15 that defines the wavelength region of the Raman-scattered light to be detected. As described above, in the present embodiment, since a filter that transmits only light having a desired wavelength is provided, it is advantageous for detecting the intensity of a signal having the desired wavelength. Furthermore, the present embodiment is advantageous from the viewpoint of extracting only information necessary for obtaining the polarization anisotropy and avoiding an increase in cost of the polarization separation element.

The present embodiment includes the intraoral insertion portion 20. Therefore, it is advantageous for the diagnosis of the tooth T of the subject. In addition, in the present embodiment, since the tooth T can be irradiated with light from one direction and the Raman-scattered light can be received in the one direction, it is also advantageous for inspection of back teeth of the subject.

In the present embodiment, it is necessary to rotate the polarizer of the polarization separation element 14 in order to measure each of the intensity of the parallel component and the intensity of the orthogonal component in the Raman-scattered light. Therefore, a predetermined measurement time is required, and a time for rotating the polarizer is required during the measurement time. Each time is sufficiently short such as several seconds, but there is a possibility that a measurement point changes due to shakes of the hand of the operator or movement of the subject during the time. This is because it is difficult to completely stop the movements of both the operator of the intraoral insertion portion 20 and the subject in actual inspection of dental caries. In the present embodiment, the detection optical system further includes the shake-compensation mechanism. Therefore, an influence of the movements of the operator and the subject on the detection result is minimized, which is advantageous from the viewpoint of preventing erroneous diagnosis of dental caries.

In the present embodiment, the individual polarization components of the Raman-scattered light are separated and detected by the rotation of the polarizer of the polarization separation element 14. As described above, in the present embodiment, it is possible to obtain the polarization dependence of the Raman-scattered light from the intensity of each polarization component of the Raman-scattered light generated from the same part and to diagnose the presence or absence of dental caries. Therefore, it is advantageous from the viewpoint of more easily configuring the dental caries detection device.

In the present embodiment, an influence of dental caries on hydroxyapatite, which is a main component of the tooth T, is detected by the polarized Raman spectroscopy. Since the carious part is detected based on the difference from the normal part caused by the polarization dependence in this manner, the present embodiment is particularly advantageous in detecting early dental caries that is difficult to find by visual observation or the like.

Second Embodiment

Hereinafter, another embodiment of the present invention will be described. In the following embodiment, for convenience of description, members having the same functions as the members in the above-described embodiment are denoted by the same reference numerals, and description thereof will not be repeated. The present embodiment is substantially the same as the first embodiment described above except that an image sensor is used as the detector 12. In the present embodiment, the detector 12 is a CMOS sensor.

Figure 8:
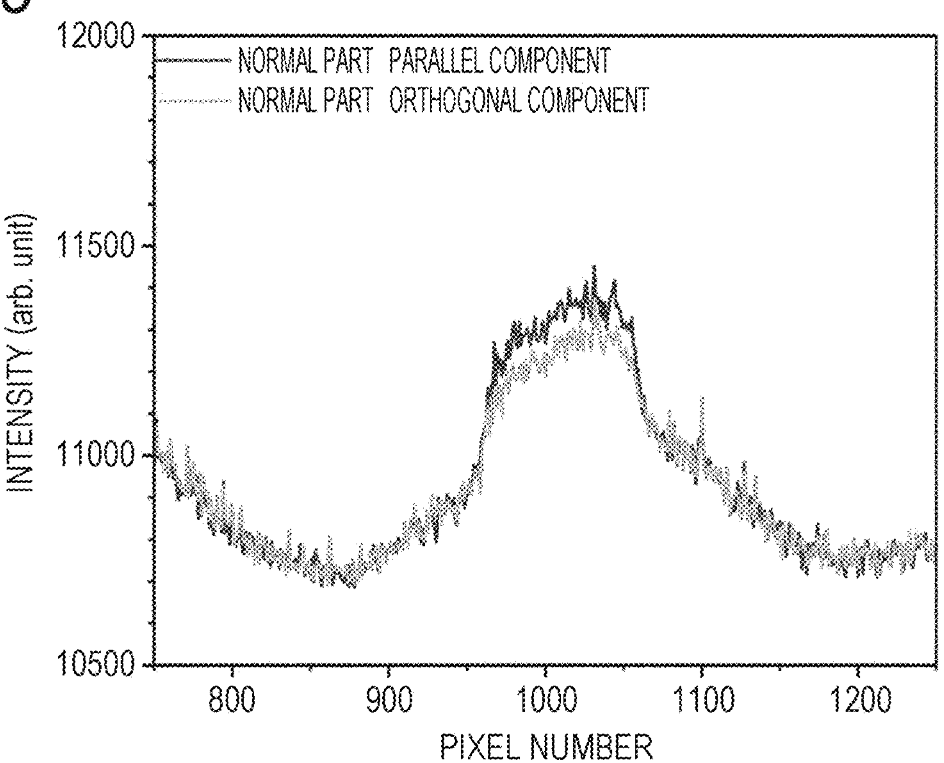
FIG. 8 is a diagram showing an example of a detection result for each polarization component at a normal part of a tooth when the tooth is analyzed by polarized Raman spectroscopy in a second embodiment of the present invention.
Figure 9:
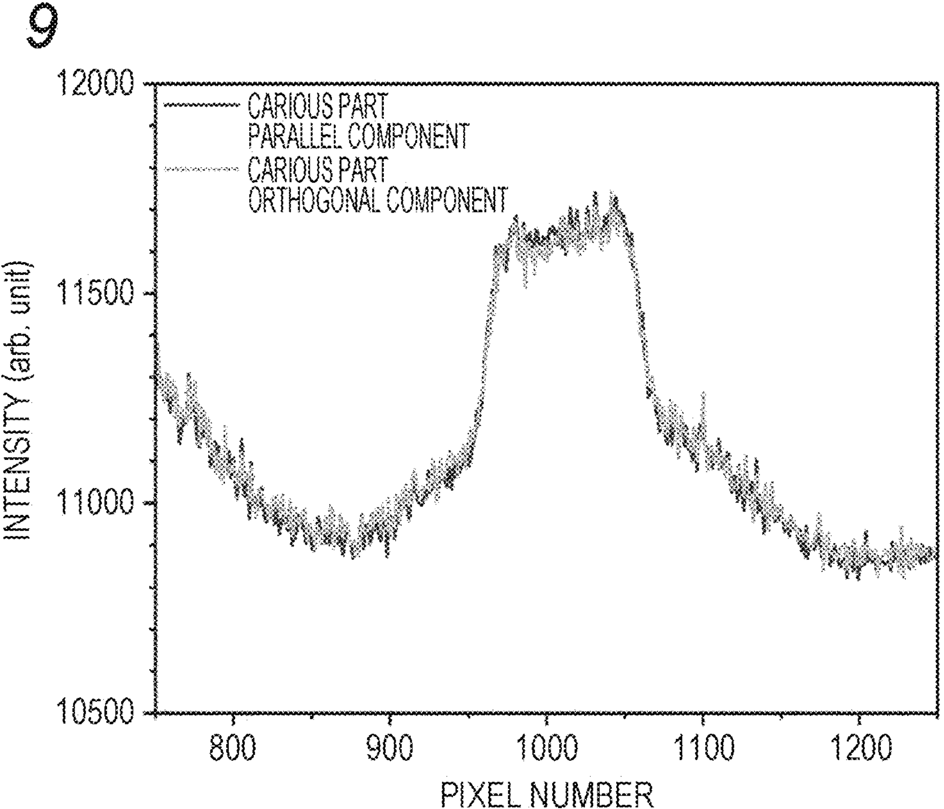
FIG. 9 is a diagram showing an example of a detection result for each polarization component at a carious part of the tooth when the tooth is analyzed by the polarized Raman spectroscopy in the second embodiment of the present invention.

FIG. 8 shows an example of a detection result for each polarization component at a normal part of a tooth T when the tooth T is analyzed by the polarized Raman spectroscopy in the present embodiment, and FIG. 9 shows an example of a detection result for each polarization component at a carious part of the tooth T.

As is clear from FIG. 8, Raman-scattered light of hydroxyapatite shows a higher intensity in a pixel number range of approximately 950 to 1050 in detection using the CMOS sensor. At the normal part, a parallel component has a higher intensity than an orthogonal component. On the other hand, at the carious part, as is clear from FIG. 9, an intensity difference between the parallel component and the orthogonal component in the range is not as large as that at the normal part, and is unclear.

Figure 10:
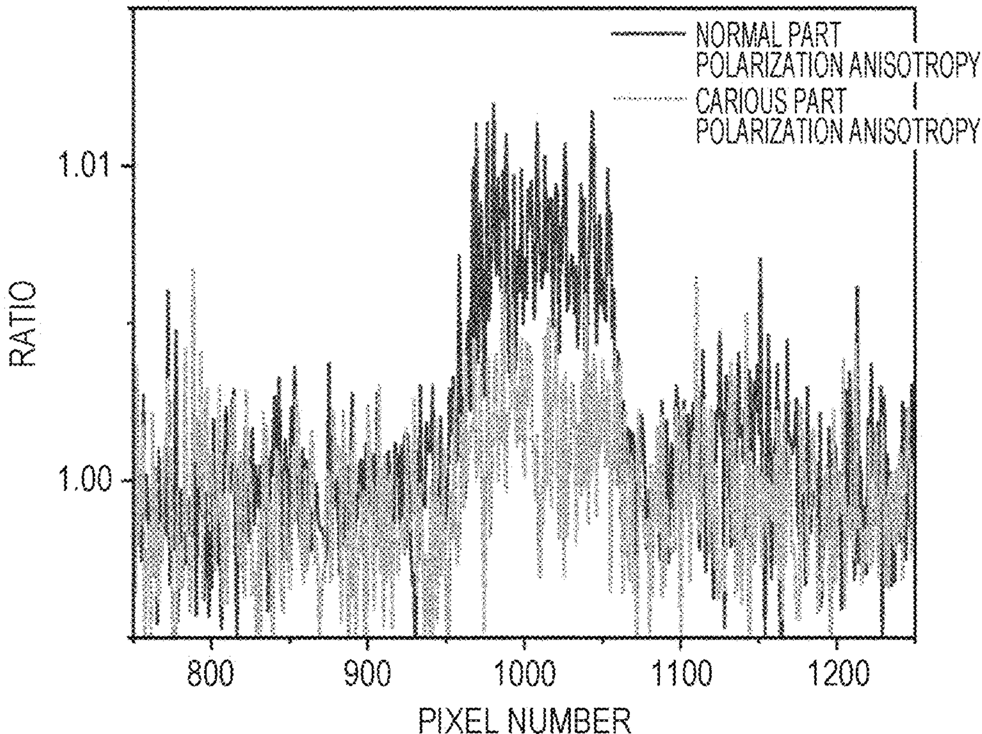
FIG. 10 is a diagram showing an example of polarization anisotropy of the normal part and polarization anisotropy of the carious part of the tooth when the tooth is analyzed by the polarized Raman spectroscopy in the second embodiment of the present invention.

FIG. 10 shows an example of polarization anisotropy of the normal part and polarization anisotropy of the carious part of the tooth when the tooth T is analyzed by the polarized Raman spectroscopy in the present embodiment. In FIG. 10, the polarization anisotropy of the normal part clearly indicates that the intensity difference between the parallel component and the orthogonal component is sufficiently larger than that at the carious part, which makes determination of the carious part easy as in the first embodiment. As described above, strong polarization dependence of a signal derived from hydroxyapatite in the polarized Raman spectroscopy for the tooth T is also shown in detection of the Raman-scattered light by the CMOS sensor.

In the present embodiment, it is not necessary to detect the dispersed Raman-scattered light by a spectrometer, which is advantageous in terms of avoiding an increase in cost of the device. In addition, a diffraction grating is not used, which is also advantageous in terms of improving efficiency in detecting the Raman-scattered light.

Third Embodiment

Figure 11:
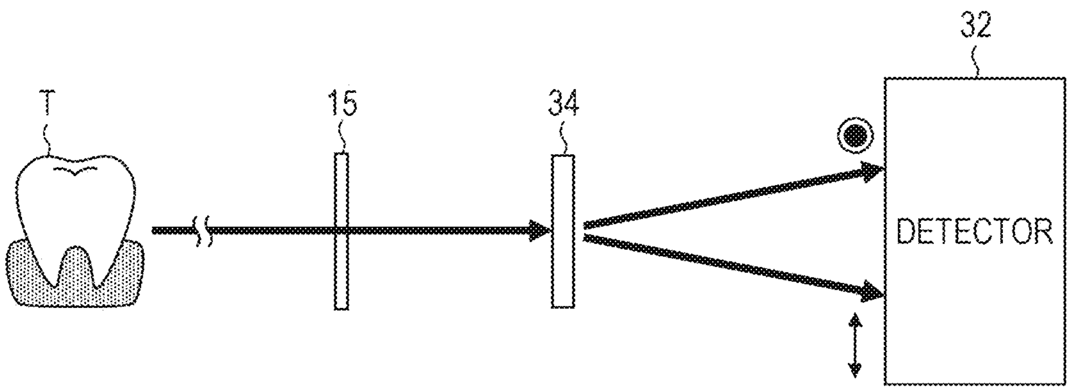
FIG. 11 is a diagram schematically illustrating a main part of a configuration of a detection optical system of a dental caries detection device according to a third embodiment of the present invention.

FIG. 11 is a diagram schematically illustrating a main part of a configuration of a detection optical system of a dental caries detection device according to a third embodiment of the present invention. The present embodiment is similar to the first embodiment described above except that a polarization separation element 34 is used instead of the polarization separation element 14, and a detector 32 is used instead of the detector 12.

The polarization separation element 34 is an optical element that separates traveling directions of light of a parallel component (first polarization component) and light of an orthogonal component (second polarization component) into different directions. That is, the polarization separation element 34 separates the parallel component and the orthogonal component in Raman-scattered light, and focuses each of the parallel component and the orthogonal component on another part of the detector 32. In this manner, the polarization separation element 34 spatially separates different polarization components. It is sufficient that the polarization separation element 34 is an optical element having a function of spatially separating different polarization components in the Raman-scattered light. Examples of the polarization separation element 34 include a Wollaston prism, a lotion prism, a polarization separation plate, a Savart plate, and a polarization separation metalens.

The detector 32 is a device that simultaneously detects each of the lights separated by the polarization separation element 34 at different focus points. The detector 32 is, for example, the above-described image sensor, and is, for example, a CMOS sensor in the present embodiment. A black circle in FIG. 11 on an upper side of the detector 32 means a polarization direction (for example, s-polarized light) of any one of the parallel component and the orthogonal component, and a double-headed arrow in FIG. 11 on a lower side of the detector 32 means a polarization direction (for example, p-polarized light) of the other one of the parallel component and the orthogonal component.

In the present embodiment, the parallel component in the Raman-scattered light is detected in, for example, the upper half of a detection region in the detector 32, and the orthogonal component in the Raman-scattered light is detected in, for example, the lower half of the detection region in the detector 32. In the present embodiment, two or more polarization components in the Raman-scattered light are simultaneously detected. Therefore, since there is less time difference in switching the polarization component by the polarization separation element 14 as compared with the embodiment described above, there is no deviation of a measurement position due to the time difference, which is advantageous from the viewpoint of enhancing the accuracy of the determination of dental caries.

Fourth Embodiment

Figure 12:
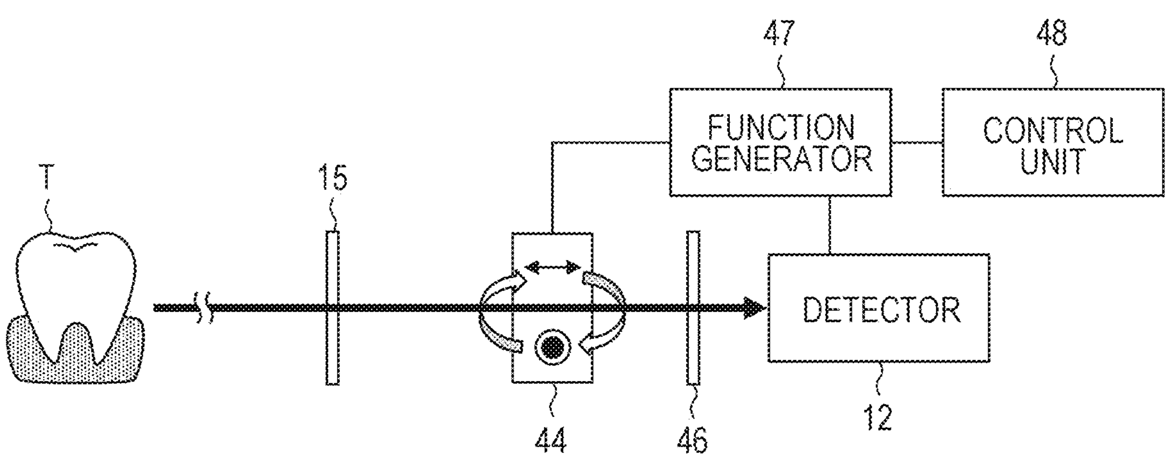
FIG. 12 is a diagram schematically illustrating a main part of a configuration of a detection optical system of a dental caries detection device according to a fourth embodiment of the present invention.

FIG. 12 is a diagram schematically illustrating a main part of a configuration of a detection optical system of a dental caries detection device according to a fourth embodiment of the present invention. The present embodiment is different from the first embodiment described above in that a photoelastic modulator 44 is used instead of the polarization separation element 14, and is otherwise similar to the first embodiment.

The dental caries detection device according to the present embodiment includes the photoelastic modulator 44 and a polarization optical element 46 in a light receiving optical system, and further includes a function generator 47 and a detection control unit 48.

The photoelastic modulator 44 is an optical element that rotates a polarization plane of Raman-scattered light. The photoelastic modulator 44 includes an optical element formed of a substance whose birefringence changes according to an applied voltage, and rotates the polarization plane of the Raman-scattered light by changing the voltage applied to the optical element.

The polarization optical element 46 is an optical element that transmits only the Raman-scattered light having a specific polarization component. Examples of the polarization optical element 46 include a wire grid polarizer, a prism polarizer, and a polarizing beam splitter.

The function generator 47 and the detection control unit 48 are devices for synchronizing the photoelastic modulator 44 and a detector 12, and are functional configurations in information processing for the synchronization. The function generator 47 and the detection control unit 48 may be built in the device main body 10, for example, or may be devices provided side by side with the device main body 10.

In the present embodiment, the polarization plane of the Raman-scattered light is switched using the photoelastic modulator 44. For example, an element that transmits only a polarization component parallel to a polarization component of laser light emitted from a light source 11 is adopted as the polarization optical element 46, and only a parallel component of the Raman-scattered light is detected by the detector 12 in a state where no voltage is applied to the photoelastic modulator 44. Next, a voltage is applied to the photoelastic modulator 44 to rotate the polarization plane of the Raman-scattered light by 90°. As a result, an orthogonal component of the Raman-scattered light is transmitted through the polarization optical element 46. The photoelastic modulator 44 and the detector 12 are synchronized, and signals are captured at a timing when no voltage is applied and a timing when a voltage is applied. In this way, the parallel component and the orthogonal component in the Raman-scattered light are alternately detected by the detector 12 in an extremely short period. Then, the above-described control unit obtains polarization anisotropy from a signal intensity of each detected component.

The photoelastic modulator 44 can modulate the polarization plane of the Raman-scattered light without rotating the optical element, and can perform the polarized Raman spectroscopy in a short time. Therefore, the photoelastic modulator 44 is advantageous in detecting a minute change for each polarization component of the Raman-scattered light. The present embodiment is more advantageous than the above-described embodiment from the viewpoint of improving the accuracy in detection of dental caries.

Fifth Embodiment

Figure 13:
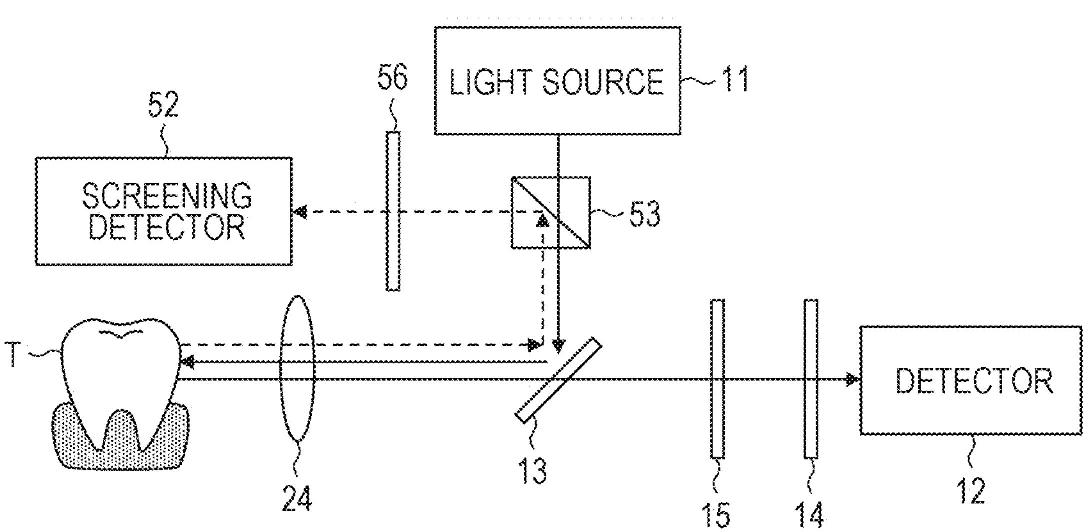
FIG. 13 is a diagram schematically illustrating a main part of a configuration of a detection optical system of a dental caries detection device according to a fifth embodiment of the present invention.

A dental caries detection device of the present embodiment further includes a screening unit that detects a suspected carious part Tc in a tooth T. FIG. 13 is a diagram schematically illustrating a main part of a configuration of a detection optical system of the dental caries detection device according to a fifth embodiment of the present invention. The dental caries detection device of the present embodiment is similar to that of the first embodiment described above except that the detection optical system further includes a screening optical filter 53, a screening polarization optical element 56, and a screening detector 52.

The screening optical filter 53 is an optical element that guides reflected light of the tooth T toward the screening detector 52. Here, the "reflected light" is light other than Raman-scattered light (transmitted through an optical filter 13) toward a detector 12 as light from the tooth T, and is light reflected by the optical filter 13. A beam splitter is used as the screening optical filter 53, and examples thereof include a half mirror and a polarizing beam splitter.

The screening polarization optical element 56 is an optical element that blocks a parallel component in the reflected light and transmits an orthogonal component. The screening polarization optical element 56 transmits the orthogonal component polarized in a direction perpendicular to the parallel component same as a polarization component of light from a light source 11 and component light in other polarization directions in the reflected light. Examples of the screening polarization optical element 56 include a wire grid polarizer, a prism polarizer, and a polarizing beam splitter.

The screening detector 52 detects light transmitted through the screening polarization optical element 56. A detector that can be used to capture a polarized photograph can be used as the screening detector 52, and examples thereof include the above-described image sensor. In the present embodiment, the screening detector 52 is, for example, a CMOS sensor.

Figure 14:
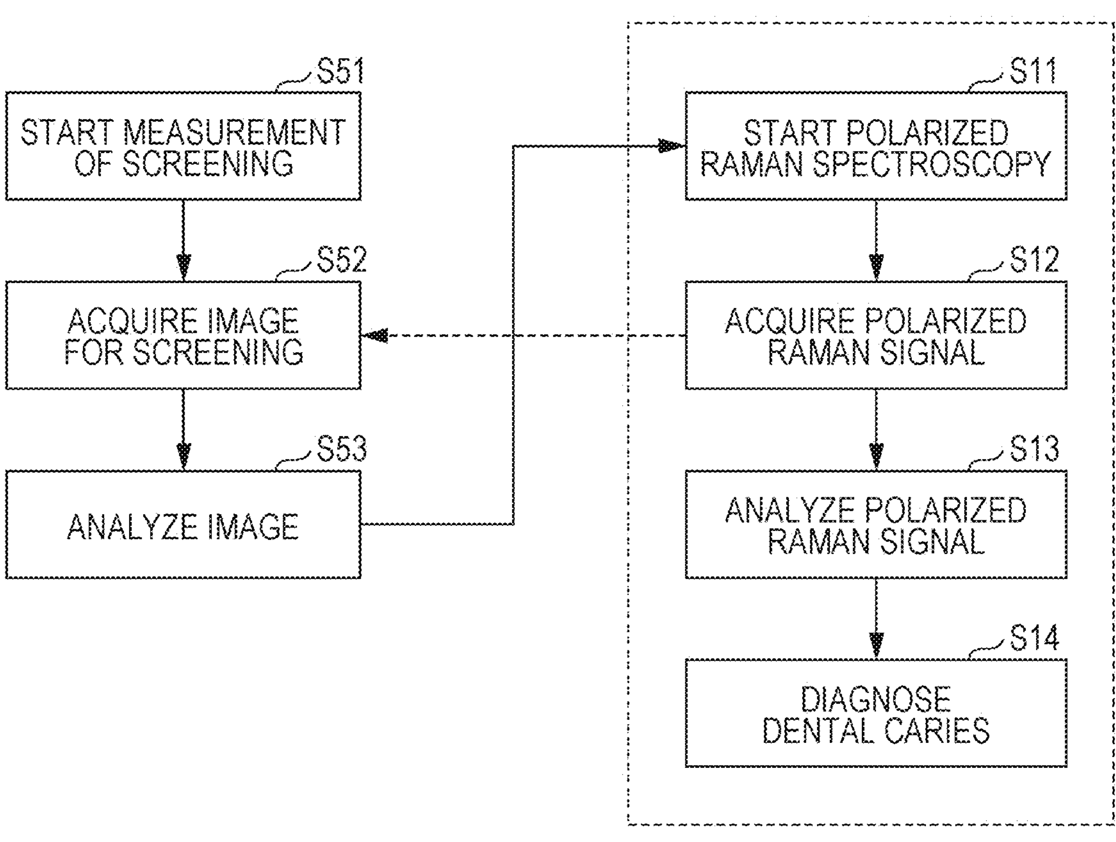
FIG. 14 is a diagram showing an example of a flow of processing of detecting dental caries in the dental caries detection device according to the fifth embodiment of the present invention.

FIG. 14 is a diagram illustrating an example of a flow of processing of detecting dental caries in the present embodiment. In the present embodiment, screening processing is further included in addition to the dental caries detection processing in the first embodiment described above. Hereinafter, the screening processing will be described.

In step S51, a control unit starts measurement of screening. For example, the control unit activates the screening detector 52 in response to a specific operation by the operator.

In step S52, the control unit forms an image of a polarized photograph of the tooth T according to a detection signal of the screening detector 52.

Figure 15:
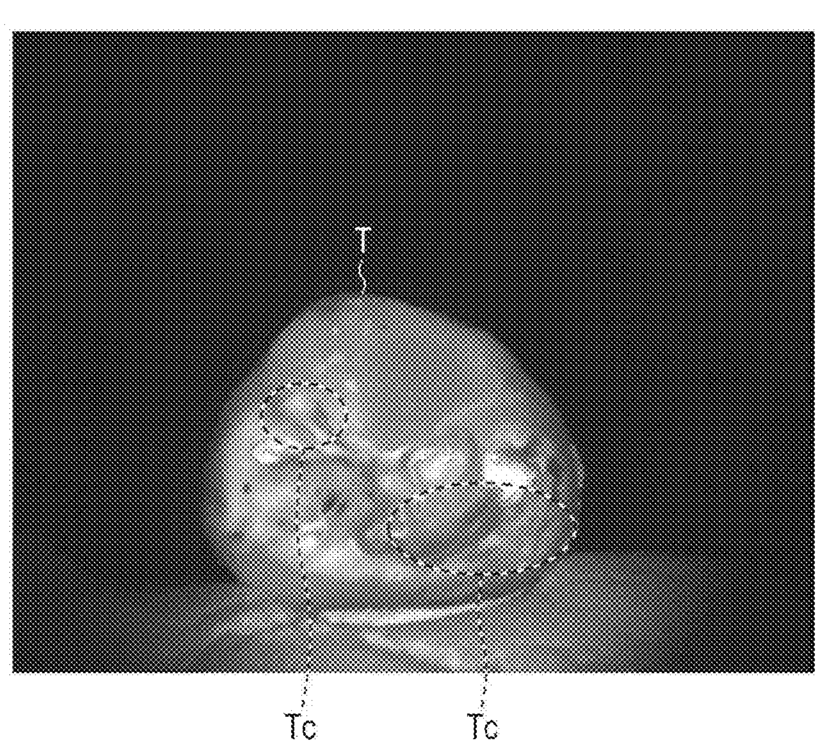
FIG. 15 is a view showing a photograph of an example of an image obtained by screening processing in the fifth embodiment of the present invention.

FIG. 15 shows an example of the image of the polarized photograph obtained in the present embodiment. With the above configuration, light of specific linearly polarized light (for example, the parallel component) in the reflected light of the tooth T is blocked, and an image including a component polarized in a direction orthogonal thereto (for example, the orthogonal component) and a component polarized in a direction other than that of the parallel component is obtained as the image of the polarized photograph of the tooth T.

When imaging is performed using such a crossed Nicols arrangement, specular reflection (halation) is removed, and a state of a surface of the tooth T can be easily observed. In the polarized photograph, the suspected carious part Tc tends to appear brighter. It is considered that this is because a structure of the tooth is disturbed in a carious part as compared with a normal part, and light is easily scattered. Therefore, a brighter portion in the polarized photograph can be determined as the suspected carious part Tc (a part suspected of having dental caries) by adding other elements such as a three-dimensional shape of the surface of the tooth T as necessary. By more intensively scanning the suspected carious part Tc in dental caries inspection, the dental caries of the tooth T can be detected more quickly and more accurately.

As described above, in the present embodiment, a reflection photograph (polarized photograph) imaged using the crossed Nicols arrangement is used for screening of the suspected carious part Tc. The specular reflection (halation) can be substantially removed by imaging the tooth T using the crossed Nicols arrangement. As a result, a part having a surface state (for example, color or roughness) slightly different due to dental caries is more clearly shown in the polarized photograph, and the suspected carious part Tc can be more easily determined.

FIG. 15 is a photograph of the extracted tooth T with dental caries, captured from a crown side. Even in a case where the tooth T is inspected in the oral cavity, a similar polarized photograph can be captured.

In step S53, the control unit analyzes the image of the polarized photograph. The control unit may extract the suspected carious part Tc from the image of the polarized photograph according to a specific condition and display the result on a display device 30. Alternatively, the control unit may display the image of the polarized photograph on the display device 30 for screening of the tooth T by a dentist.

In the present embodiment, the operator specifies the suspected carious part Tc in the tooth T by the screening, and detects dental caries in the tooth T based on the screening result. In the present embodiment, the acquisition of the image for screening in step S52 and the acquisition of the polarized Raman signal in step S12 may be repeatedly performed as necessary as indicated by a dashed arrow in FIG. 14.

By repeating such steps, it is possible to refer to a measurement position after performing the polarized Raman spectroscopy. Therefore, in the present embodiment, the measurement position can be confirmed based on a screening image before and after the polarized Raman spectroscopy, and as a result, in the present embodiment, it is advantageous in preventing erroneous diagnosis due to measurement of a position different from the assumed position. In addition, the repetition of the above steps is effective from the viewpoint of specifying a more effective range as a scanning range of the tooth T for detecting dental caries since the position of the suspected carious part Tc in the tooth T can be confirmed.

Sixth Embodiment

Figure 16:
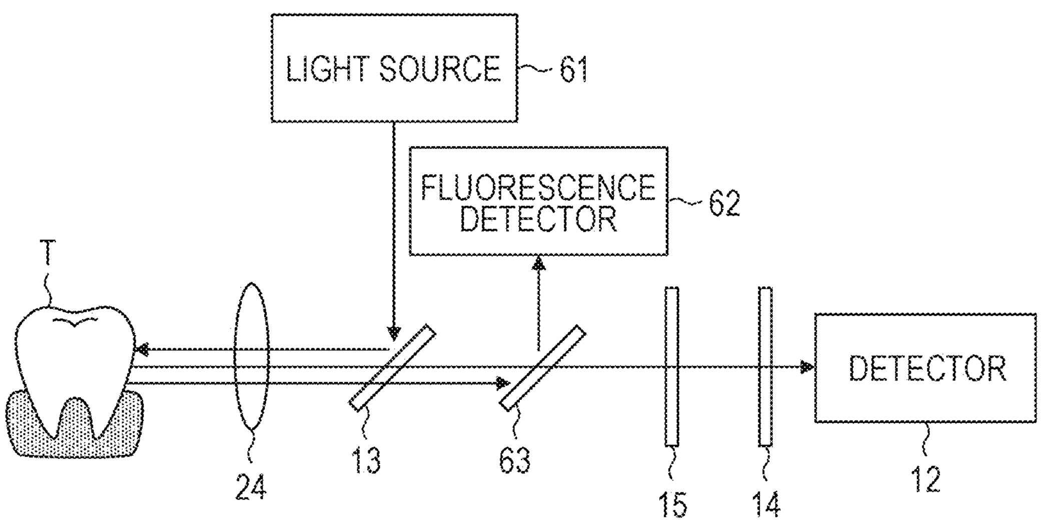
FIG. 16 is a diagram schematically illustrating a main part of a configuration of a detection optical system of a dental caries detection device according to a sixth embodiment of the present invention.

Similarly to the fifth embodiment, a dental caries detection device of the present embodiment further includes a screening unit that detects a suspected carious part Tc in a tooth T. FIG. 16 is a diagram schematically illustrating a main part of a configuration of a detection optical system of the dental caries detection device according to a sixth embodiment of the present invention. The dental caries detection device of the present embodiment is similar to that of the first embodiment described above except that a light source 61 is included instead of the light source 11, and the detection optical system further includes a fluorescence separation element 63 and a fluorescence detector 62.

Similarly to the light source 11, the light source 61 emits light (excitation light) that generates Raman-scattered light when irradiating the tooth T and further excites fluorescence generated from a carious part of the tooth T. It is known that dental caries is progressed by acid produced by cariogenic bacteria, and at this time, a substance called porphyrin is produced as a by-product of metabolism. Therefore, there is a possibility that cariogenic bacteria exist and dental caries occurs in a place where the porphyrin exists. It is also known that the porphyrin is excited by red light and emits red fluorescence having a longer wavelength than excitation light. The “fluorescence” in the present embodiment is fluorescence of a fluorescent component generated by dental caries, and examples thereof include the red fluorescence of porphyrin described above.

As the excitation light generated by the light source 61, for example, a visible ray or near-infrared ray having a partial wavelength in a wavelength range of 300 to 800 nm can be applied according to an excitation wavelength of a target fluorescence component. It is sufficient if the excitation light of porphyrin is light having a wavelength shorter than the wavelength of the fluorescence of porphyrin. In the present embodiment, for light that generates the Raman-scattered light and the excitation light, a laser having a wavelength of 633 nm can be adopted as the light source 61. As described above, the light source 61 also serves as a fluorescence light source that emits the excitation light. The light source 61 may be a wavelength-tunable light source, or may be a plurality of light sources corresponding to each of the light that generates the Raman-scattered light and the excitation light described above.

The fluorescence separation element 63 is an optical element that reflects the fluorescence from the tooth T toward the fluorescence detector 62. Examples of the fluorescence separation element 63 include an edge filter, a notch filter, and a dichroic mirror.

The fluorescence detector 62 is a detector that detects the fluorescence from the tooth T. Examples of the fluorescence detector 62 include a CMOS sensor, a CCD sensor, a photomultiplier tube, and a photodiode. In the present embodiment, the fluorescence detector 62 is, for example, an image sensor, and is a CMOS sensor.

In the present embodiment, an optical filter 13 is designed to reflect the light (excitation light) from the light source 61 and transmit light having a longer wavelength than the excitation light.

The polarized Raman-scattered light specific to the suspected carious part Tc and the red fluorescence derived from porphyrin in the light reflected and scattered by the suspected carious part Tc are transmitted through the optical filter 13 and reach the fluorescence separation element 63. The red fluorescence derived from porphyrin is reflected by the fluorescence separation element 63 toward the fluorescence detector 62, and the remaining polarized Raman-scattered light is detected by a detector 12 via a bandpass filter 15 and a polarization separation element 14. A control unit forms an image of the tooth T including the red fluorescence derived from porphyrin from data of the fluorescence detected by the fluorescence detector 62, and displays the image on a display device 30.

Figure 17:
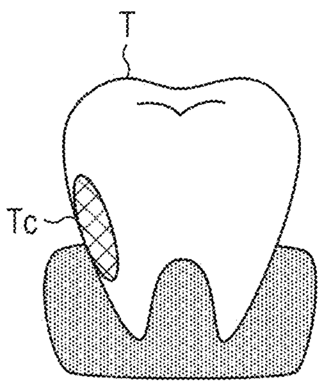
FIG. 17 is a view schematically illustrating an example of an image obtained by screening processing in the sixth embodiment of the present invention.

FIG. 17 is a diagram schematically illustrating an example of an image obtained by screening processing in the present embodiment. In the present embodiment, as described above, the image of the tooth T is obtained. For example, in a case where the tooth T has the suspected carious part Tc at a boundary portion with the gum, the image of the tooth T having a region of the red fluorescence derived from porphyrin at the boundary portion is obtained. By capturing a photograph of the tooth T including such a region of the red fluorescence, it is possible to determine a region where porphyrin exists as the suspected carious part Tc, that is, a part suspected of having dental caries.

Also in the present embodiment, similarly to the fifth embodiment, it is possible to confirm whether or not a measurement position for the polarized Raman spectroscopy in the tooth T is appropriate based on the screening image. In the present embodiment, since the screening is performed based on fluorescence of a component derived from the activity of cariogenic bacteria, there is a high possibility that the suspected carious part Tc where the fluorescence is detected is actually a carious part. Therefore, the present embodiment is more effective than the above-described fifth embodiment from the viewpoint of more accurately specifying the measurement point for the polarized Raman spectroscopy from the screening image.

Other Embodiments

A dental caries detection device according to the present invention may further include an intraoral 3D scanning device that forms a three-dimensional image of the inside of the oral cavity of a subject. According to the embodiment, it is possible to form a three-dimensional image of the oral cavity of the subject reflecting results of dental caries detection and screening in the above-described embodiments. The present embodiment is effective from the viewpoint of promoting digitization of a dental chart of a subject, and enrichment and utilization of such an electronic medical chart.

In addition, each processing described in the embodiments of the present invention may be executed by artificial intelligence (AI). For example, in the embodiments of the present invention, AI may be caused to determine the suspected carious part, determine the carious part, or diagnose dental caries. Further, it is expected that sufficiently useful results for the suspected carious part, the carious part, and the diagnosis thereof are brought about by AI based on the knowledge of quantitative evaluation. In the embodiments of the present invention, AI may operate in the control unit, or may operate in another device (for example, an edge computer or a cloud server).

In the present invention, a focus position of light from the light source on the tooth T may be corrected during the polarized Raman spectroscopy. Such an embodiment is also effective from the viewpoint of suppressing the influence of the shakes of the hand of the operator and preventing erroneous dental caries diagnosis. The embodiment can be implemented by using a variable-focus lens, such as a liquid lens, as a focusing lens (for example, the lens 24) in the detection optical system, and the above-described control unit controlling the focal length of the lens according to a detected value of the gyro sensor described above. Further, with the configuration in which the focal length of irradiation light for the tooth T can be changed, an irradiation range of the irradiation light for the tooth T can be changed. Therefore, it is possible to continuously change the irradiation range of the irradiation light from the entire tooth T to the suspected carious part Tc. Therefore, it is advantageous from the viewpoint of enabling both screening diagnosis and dental caries diagnosis with the same device configuration.

Modified Example

In the fifth embodiment, the light source 11 may emit rays of light having different wavelengths as light for obtaining the polarization anisotropy by the polarized Raman spectroscopy and light for capturing the polarized photograph for screening. Since the light for capturing the polarized photograph only needs to be able to capture the polarized photograph, light having an arbitrary wavelength in a wavelength range from a visible ray to a near-infrared ray can be selected as the light for capturing the polarized photograph.

In the present invention, screening in which both the screening of the fifth embodiment (polarized photograph) and the screening of the sixth embodiment (fluorescence detection) are combined may be adopted. Such an embodiment is advantageous from the viewpoint of further enhancing the accuracy of screening for a carious part.

Further, in the fifth embodiment or the sixth embodiment, in a case where the measurement position before and after the polarized Raman spectroscopy is referred to, deviation of the measurement position may be obtained from a difference between images before and after the polarized Raman spectroscopy. Such a configuration is also effective from the viewpoint of reducing an influence of movements of the operator and the subject during the measurement and from the viewpoint of preventing erroneous diagnosis due to the influence of the movements.

Summary

As the life expectancy of human beings is extending worldwide, extending the healthy life expectancy, which is a period during which people can live without requiring nursing care, has become an important social issue. As a result of research and studies so far, elderly people with a large number of teeth tend to have a long healthy life expectancy. In addition, dental caries and a periodontal disease constitute a significant portion of the factors contributing to tooth loss. Therefore, how to prevent the periodontal disease is important.

Meanwhile, in the polarized Raman spectroscopy in which polarization information is also obtained in addition to wavelength information of the Raman-scattered light, it is possible to evaluate the polarization dependence of the detected intensity of the Raman-scattered light. This is effective for evaluating a substance having a specific molecular orientation, such as a polymer material or a crystal. As for the tooth inspection, hydroxyapatite, which is a main component of a tooth, has crystallinity and has a specific orientation of constituent molecules, and thus is suitable for detecting the polarization dependence based on the Raman-scattered light.

Meanwhile, in dental caries of the tooth, hydroxyapatite is dissolved by acid. Therefore, the crystallinity of hydroxyapatite decreases, and the polarization dependence of the intensity of the Raman-scattered light decreases at the carious part of the tooth. Various deposits adhere to teeth and usually do not have crystallinity. Therefore, the polarization dependence of the intensity of the Raman-scattered light tends not to be usually observed from the deposits.

In the present invention, it is possible to easily extract information of hydroxyapatite and detect the presence of dental caries by performing the polarized Raman spectroscopy at the same measurement point in the tooth and evaluating the polarization dependence of the Raman-scattered light. Furthermore, quantitative evaluation of the progress of dental caries is also expected. In the present invention, it is possible to easily interpret a Raman spectrum for evaluating the progress of dental caries by performing the polarized Raman spectroscopy.

In addition, as the function of substantially simultaneously measuring intensities of a plurality of polarization components is provided in the present invention, the intensity of each polarization component of the Raman-scattered light generated from the same point can be evaluated, and the measurement time can be shortened and the measurement accuracy can be improved.

Furthermore, it is usually difficult for a dentist who needs to perform inspection and diagnosis and a patient with dental caries not to make any movement other than required movement during the inspection. For example, it may be difficult to sufficiently fix the measurement position due to slight movement of the measurement position caused by movement of the patient during the polarized Raman spectroscopy, shakes of the arm of the operator, or the like. Such unintended movement leads to a decrease in accuracy of the dental caries diagnosis. In the present invention, a configuration capable of position correction such as image stabilization is further adopted, so that it is possible to minimize the deviation of the measurement position and to further improve the diagnosis accuracy, and as a result, it is possible to prevent erroneous diagnosis.

According to a first aspect of the present invention, a dental caries detection device includes: a light source (11) configured to emit light having a first polarization direction; a polarization separation unit (polarization separation element 14) configured to separate the light having the first polarization direction and other light having a second polarization direction in Raman-scattered light from a tooth (T) of a subject irradiated with the light having the first polarization direction; a detector (12) configured to detect each of the light having the first polarization direction and the light having the second polarization direction separated by the polarization separation unit; and an anisotropy acquisition unit configured to obtain polarization anisotropy of the Raman-scattered light from a detection signal of each of the light having the first polarization direction and the light having the second polarization direction from the detector. According to the first aspect, it is possible to clearly and easily detect dental caries when diagnosing dental caries by Raman spectroscopy.

According to a second aspect of the present invention, in the first aspect, the polarization separation unit is an optical element (polarization separation element 34) that separates traveling directions of the light having the first polarization direction and the light having the second polarization direction into different directions. The second aspect is more effective from the viewpoint of improving the accuracy in determination of dental caries.

According to a third aspect of the present invention, in the first aspect, the polarization separation unit is a photoelastic modulator (44) that rotates a polarization plane. The third aspect is more effective from the viewpoint of improving the accuracy in detection of dental caries.

According to a fourth aspect of the present invention, in any one of the first to third aspects, the dental caries detection device further includes an intraoral insertion portion (20) including at least a part of an optical system from the light source to the detector and configured to be insertable into an oral cavity of the subject, in which the optical system further includes a shake-compensation mechanism. The fourth aspect is more effective from the viewpoint of being applied to dental caries diagnosis for the subject.

According to a fifth aspect of the present invention, in any one of the first to fourth aspects, the dental caries detection device further includes a bandpass filter (15) configured to transmit light having a specific wavelength in the Raman-scattered light. The fifth aspect is more effective from the viewpoint of avoiding an increase in cost of the polarization separation element.

According to a sixth aspect of the present invention, in any one of the first to fifth aspects, the dental caries detection device further includes a screening unit configured to detect a suspected carious part (Tc) in the tooth. The sixth aspect is more effective from the viewpoint of confirming suitability of the measurement position for the polarized Raman spectroscopy.

According to a seventh aspect of the present invention, in the sixth aspect, the screening unit includes: a screening polarization optical element (56) configured to block the light having the first polarization direction and transmits the light having the second polarization direction in reflected light from the tooth irradiated with the light having the first polarization direction; and a screening detector (52) configured to detect the light transmitted through the screening polarization optical element. The seventh aspect is more effective from the viewpoint of clearly showing a part having a different state due to dental caries in the tooth and easily determining the suspected carious part.

According to an eighth aspect of the present invention, in the sixth or seventh aspect, the screening unit includes a fluorescence light source (light source 61) configured to emit excitation light with which the tooth is to be irradiated, and a fluorescence detector (62) configured to detect fluorescence from the tooth irradiated with the excitation light. The eighth aspect is more effective from the viewpoint of accurately specifying the measurement point (suspected carious part) for the polarized Raman spectroscopy from the screening image.

According to a ninth aspect of the present invention, in any one of the first to eighth aspects, the dental caries detection device further includes an intraoral 3D scanning device configured to form a three-dimensional image of the inside of the oral cavity of the subject. The ninth aspect is more effective from the viewpoint of promoting digitization, enrichment, and utilization of dental information of the subject.

With the above-described configurations in the embodiments of the present invention, it is possible to accurately, quickly, and easily detect dental caries and periodontal diseases from an early stage. Therefore, according to the embodiments of the present invention, it is expected that early detection of periodontal diseases will lead to extension of healthy life expectancy, and for example, it is expected to contribute to achievement of Coal 3 of the sustainable development goal (SDGs) proposed by the United Nations, which is to "ensure healthy lives and promote well-being for all at all ages", and the like.

The present invention is not limited to the above-described embodiments, and various modifications can be made within the scope of the claims. Embodiments obtained by combining as appropriate technical means disclosed in relation to different embodiments are also included in the technical scope of the present invention.

What is claimed is:

1. A dental caries detection device comprising:

a light source configured to emit light having a first polarization direction;

a polarization separation unit configured to separate the light having the first polarization direction and other light having a second polarization direction in Raman-scattered light from a tooth of a subject irradiated with the light having the first polarization direction;

a detector configured to detect each of the light having the first polarization direction and the light having the second polarization direction separated by the polarization separation unit; and an anisotropy acquisition unit configured to obtain polarization anisotropy of the Raman-scattered light by obtaining a detection signal of each of the light having the first polarization direction and the light having the second polarization direction from the detector and analyzing the detection signal.

2. The dental caries detection device according to claim 1, wherein the polarization separation unit is an optical element that separates traveling directions of the light having the first polarization direction and the light having the second polarization direction into different directions.

3. The dental caries detection device according to claim 1, wherein the polarization separation unit is a photoelastic modulator that rotates a polarization plane.

4. The dental caries detection device according to claim 1, further comprising an intraoral insertion portion including at least a part of a detection optical system from the light source to the detector and configured to be insertable into an oral cavity of the subject, wherein the detection optical system further includes a shake-compensation mechanism.

5. The dental caries detection device according to claim 1, further comprising a bandpass filter configured to transmit light having a specific wavelength in the Raman-scattered light.

6. The dental caries detection device according to claim 1, further comprising a screening unit configured to detect a suspected carious part in the tooth.

7. The dental caries detection device according to claim 6, wherein the screening unit includes:

a screening polarization optical element configured to block the light having the first polarization direction and transmit the light having the second polarization direction in reflected light from the tooth irradiated with the light having the first polarization direction; and a screening detector configured to detect the light transmitted through the screening polarization optical element.

8. The dental caries detection device according to claim 6, wherein the screening unit includes:

a fluorescence light source configured to emit excitation light; and a fluorescence detector configured to detect fluorescence from the tooth irradiated with the excitation light.

9. The dental caries detection device according to claim 1, further comprising an intraoral 3D scanning device configured to form a three-dimensional image of an inside of an oral cavity of the subject.

10. The dental caries detection device according to claim 1, wherein the detector is a single detector configured to detect each of the light having the first polarization direction and the light having the second polarization direction separated by the polarization separation unit.

11. The dental caries detection device according to claim 1, wherein the polarization separation unit is a photoelastic modulator that rotates a polarization plane by an applied voltage.

12. The dental caries detection device according to claim 11, further comprising a function generator and a detection control unit for synchronizing the photoelastic modulator and the detector.

* * * * *